US009119820B2

(12) United States Patent
Fukushima et al.

(10) Patent No.: US 9,119,820 B2
(45) Date of Patent: Sep. 1, 2015

(54) TABLET QUICKLY DISINTEGRATING IN THE ORAL CAVITY AND METHOD FOR PRODUCING THE SAME

(75) Inventors: Toru Fukushima, Osaka (JP); Takashi Shimizu, Ibaraki (JP); Teruko Yoshida, Ibaraki (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 592 days.

(21) Appl. No.: 12/997,779

(22) PCT Filed: Jun. 10, 2009

(86) PCT No.: PCT/JP2009/060584
§ 371 (c)(1),
(2), (4) Date: Dec. 13, 2010

(87) PCT Pub. No.: WO2009/151072
PCT Pub. Date: Dec. 17, 2009

(65) Prior Publication Data
US 2011/0105615 A1    May 5, 2011

(30) Foreign Application Priority Data

Jun. 13, 2008  (JP) ................................ 2008-155300

(51) Int. Cl.
*A61K 31/198* (2006.01)
*A61K 47/38* (2006.01)
*A61K 47/36* (2006.01)
*A61K 9/20* (2006.01)
*A61K 9/00* (2006.01)

(52) U.S. Cl.
CPC ............. *A61K 31/198* (2013.01); *A61K 9/0056* (2013.01); *A61K 9/2018* (2013.01); *A61K 9/2059* (2013.01)

(58) Field of Classification Search
CPC ..... A61K 31/198; A61K 47/38; A61K 47/36; A61K 9/20
USPC .......................... 514/567, 772.5, 778; 264/109
See application file for complete search history.

(56) References Cited

U.S. PATENT DOCUMENTS

| 3,920,728 | A | 11/1975 | Hegedus et al. | |
| 6,287,596 | B1 * | 9/2001 | Murakami et al. | ............ 424/464 |
| 6,339,104 | B1 * | 1/2002 | Nishiguchi et al. | ............ 514/561 |
| 2002/0177593 | A1 | 11/2002 | Ishihara et al. | |
| 2003/0026835 | A1 | 2/2003 | Nishii et al. | |
| 2003/0086967 | A1 | 5/2003 | Morita et al. | |
| 2003/0129226 | A1 | 7/2003 | Liu et al. | |
| 2004/0028741 | A1 | 2/2004 | Fujihara | |
| 2007/0048363 | A1 | 3/2007 | Salama | |
| 2008/0095838 | A1 | 4/2008 | Chacra-Vernet | |
| 2009/0074861 | A1 | 3/2009 | Ochiai et al. | |
| 2009/0143404 | A1 | 6/2009 | Fujihara | |

FOREIGN PATENT DOCUMENTS

| EP | 0 887 078 A1 | 12/1998 |
| EP | 2 050 448 A1 | 4/2009 |
| JP | 50-049252 A | 5/1975 |
| JP | 52-125630 A | 10/1977 |
| JP | 08-059490 A | 3/1996 |
| JP | 2002-506811 A | 3/2002 |
| JP | 2002-363067 A | 12/2002 |
| JP | 2003-095928 A | 4/2003 |
| JP | 2005-533802 A | 11/2005 |
| JP | 2007-508331 A | 4/2007 |
| WO | WO 00/47233 A1 | 8/2000 |
| WO | WO 01/64190 A1 | 9/2001 |
| WO | WO 01/76565 A1 | 10/2001 |
| WO | WO 02/24166 A1 | 3/2002 |
| WO | WO 2004/100929 A1 | 11/2004 |
| WO | WO 2006/123678 A1 | 11/2006 |
| WO | WO 2006/126681 A1 | 11/2006 |
| WO | WO 2006/128022 A2 | 11/2006 |
| WO | WO 2008/018371 A1 | 2/2008 |

OTHER PUBLICATIONS

Takagi et al., *European Neuropsychoparmacology*, 6: 43-47 (1996).
Japanese Patent Office, Notice of Reasons for Refusal in Japanese Patent Application No. 2007/516308 (Mar. 21, 2012).
Japanese Patent Office, Notice of Reasons for Refusal in Japanese Patent Application No. 2009/130801 (Mar. 21, 2012).

(Continued)

*Primary Examiner* — Kendra D Carter
*Assistant Examiner* — Jason A Deck
(74) *Attorney, Agent, or Firm* — Leydig, Voit & Mayer, Ltd.

(57) ABSTRACT

The present invention relates to a tablet which is rapidly disintegrated in an oral cavity containing an active ingredient at a high content and a production method thereof. That is, the present invention provides a tablet which is rapidly disintegrated in an oral cavity containing an active ingredient in not less than 25% of the total weight, having a disintegration time of within 40 seconds and an absolute hardness of 1.8 N/mm$^2$ or more, which is obtained by granulating a powder containing an active ingredient with a binding solution containing mannitol and corn-derived pregelatinized starch, mixing the resulting granules with at least one kind of a disintegrant selected from cornstarch, hydroxypropylstarch, carmellose and crospovidone, and compression molding the mixture.

20 Claims, No Drawings

(56) References Cited

OTHER PUBLICATIONS

Chinese State Intellectual Property Office, First Office Action in Chinese Patent Application No. 200680017202.0 (Sep. 25, 2009).
Chinese State Intellectual Property Office, Second Office Action in Chinese Patent Application No. 200680017202.0 (Dec. 9, 2010).
European Patent Office, Extended European Search Report in European Patent Application No. 06746504.7 (May 13, 2009).
European Patent Office, Office Action in European Patent Application No. 06746504.7 (Aug. 3, 2009).
Japanese Patent Office, International Search Report in International Patent Application No. PCT/JP2006/309801 (Jun. 27, 2006).
Japanese Patent Office, International Search Report in International Patent Application No. PCT/JP2009/060584 (Sep. 8, 2009).
Chinese Patent Office, First Office Action in Chinese Patent Application No. 200980131311.9 (Mar. 14, 2012).

* cited by examiner

TABLET QUICKLY DISINTEGRATING IN THE ORAL CAVITY AND METHOD FOR PRODUCING THE SAME

TECHNICAL FIELD

The present invention relates to an orally disintegrating tablet containing an active ingredient at a high concentration and having good oral disintegratability and sufficient strength for handling, and a production method thereof.

BACKGROUND ART

While various orally disintegrating tablets and production methods thereof are heretofore known, achievement of good disintegrability and tablet strength is difficult since the both properties are conflicting. In recent years, moreover, the desired level of tablet strength has become high, since the tablet should not break during production and distribution processes, as well as stand the packaging by automatic packaging machines in pharmacy and the like. Particularly, a tablet which is rapidly-disintegrated in an oral cavity having a high content of an active ingredient faces difficulty in affording both superior rapid-disintegrability in an oral cavity and superior tablet strength, since it can contain only reduced amounts of excipient, disintegrant and the like to be added besides an active ingredient, which contribute to the good rapid-disintegrability and sufficient strength, so as to produce a tablet with an easily ingestible size.

As a tablet which is rapidly disintegrated in an oral cavity having a high active ingredient content percentage, a tablet containing droxidopa as an active ingredient, and mannitol and cornstarch is known (see patent document 1). In addition, a tablet which is rapidly disintegrated in an oral cavity containing polaprezinc as an active ingredient, and mannitol, hydroxypropylstarch and crospovidone (trade name: Promac D tablets 75) has been reported. However, a tablet superior in both the rapid-disintegrability in an oral cavity and tablet strength, as well as a production method thereof have been further desired.

[patent document 1] WO 06/123678
[patent document 2] WO 00/047233

SUMMARY OF THE INVENTION

Problem to be Solved by the Invention

The problem to be solved by the present invention is provision of a tablet which is rapidly disintegrated in an oral cavity containing an active ingredient at a high concentration, and having both good disintegrability in the oral cavity and tablet strength sufficient to apply automatic packaging machines, and a production method thereof.

Means of Solving the Problem

The present inventors have conducted intensive studies and found that a tablet having, in combination, superior rapid-disintegrability in an oral cavity and sufficient strength for distribution and handling can be obtained by granulating a powder containing an active ingredient with a binding solution containing mannitol and corn-derived pregelatinized starch, adding at least one kind of disintegrant selected from cornstarch, hydroxypropylstarch, carmellose and crospovidone to the granules, and further compression molding of the mixture, which resulted in the completion of the present invention.

Accordingly, the present invention relates to

[1] a tablet, which is rapidly disintegrated in an oral cavity, comprising an active ingredient in not less than 25% of the total weight, which is obtained by compression molding a mixture comprising a granule comprising the active ingredient, mannitol and corn-derived pregelatinized starch, and at least one kind of disintegrant selected from the group consisting of cornstarch, hydroxypropylstarch, carmellose and crospovidone;

[2] the tablet, which is rapidly disintegrated in an oral cavity, of [1], further having a disintegration time of within 40 seconds and an absolute hardness of 1.8 N/mm$^2$ or more, which is obtained by compression molding of a mixture of a granule produced by granulating a powder containing the active ingredient with a binding solution containing mannitol and corn-derived pregelatinized starch, and at least one kind of disintegrant selected from the group consisting of cornstarch, hydroxypropylstarch, carmellose and crospovidone;

[3] the tablet, which is rapidly disintegrated in an oral cavity, of [1] or [2], wherein the absolute hardness is 2.0 N/mm$^2$ or more;

[4] the tablet, which is rapidly disintegrated in an oral cavity, of any of [1] to [3], wherein the disintegrant is cornstarch or hydroxypropylstarch;

[5] the tablet, which is rapidly disintegrated in an oral cavity, of any of [1] to [4], wherein the powder comprises the active ingredient and mannitol;

[6] the tablet, which is rapidly disintegrated in an oral cavity, of any of [1] to [5], comprising the active ingredient in not less than 40% of the total weight;

[7] the tablet, which is rapidly disintegrated in an oral cavity, of [6], comprising the active ingredient in 40%-70% of the total weight;

[8] the tablet, which is rapidly disintegrated in an oral cavity, of any of [1] to [7], wherein the active ingredient is droxidopa or levodopa;

[9] a method of producing a tablet, which is rapidly disintegrated in an oral cavity, comprising an active ingredient in not less than 25% of the total weight, which method comprises the following steps:
(1) a step of granulating a powder comprising the active ingredient with a binding solution comprising mannitol and corn-derived pregelatinized starch to produce a granule containing the active ingredient;
(2) a step of mixing the granule comprising the active ingredient obtained in (1) with at least one kind of disintegrant selected from the group consisting of cornstarch, hydroxypropylstarch, carmellose and crospovidone; and
(3) a step of compression molding of a pre-tableting composition comprising the mixture obtained in (2);

[10] the production method of the tablet, which is rapidly disintegrated in an oral cavity, of [9], comprising the following steps:
(1) a step of granulating a powder comprising the active ingredient with a binding solution comprising mannitol and corn-derived pregelatinized starch to produce a granule containing the active ingredient;
(2) a step of mixing the granule comprising the active ingredient obtained in (1) with at least one kind of disintegrant selected from the group consisting of cornstarch, hydroxypropylstarch, carmellose and crospovidone; and
(3) a step of compression molding of the mixture obtained in (2);

[11] the production method of [9] or [10], wherein a disintegration time of the tablet, which is rapidly disintegrated in an oral cavity, is 40 seconds or less, and an absolute hardness thereof is 1.8 N/mm$^2$ or more;

[12] the production method of any of [9] to [11], comprising compression molding by an external lubrication method;

[13] the production method of any of [9] to [12], wherein the absolute hardness of the tablet, which is rapidly disintegrated in an oral cavity, is 2.0 N/mm$^2$ or more;

[14] the production method of any of [9] to [13], wherein the active ingredient is droxidopa or levodopa.

Effect of the Invention

The present invention has made it possible to provide a tablet which is rapidly disintegrated in an oral cavity having good disintegrability and sufficient strength in combination, and comprising an active ingredient at a high concentration. That is, the tablet which is rapidly disintegrated in an oral cavity of the present invention comprising an active ingredient at a high concentration has an appropriate size permitting easy ingestion and is superior in rapid-disintegrability in an oral cavity and strength. Therefore, it can particularly improve compliance of children and elderly people with a decreased swallowing ability.

MODE FOR CARRYING OUT THE INVENTION

The mannitol to be used in the present invention is not particularly limited, and can be used those described in "the Japanese Pharmacopoeia" or "Japanese Pharmaceutical Excipients".

While the average particle size of mannitol is not particularly limited, it is preferably 10-200 µm, more preferably 10-100 µm, further preferably 10-50 µm. Examples of the measurement method of the particle size include a method using a laser diffraction-scattering type particle size distribution measuring apparatus for measuring a particle size of a micrometer order, and a method using a dynamic light scattering type particle size distribution measuring apparatus for measuring a particle size of a nanometer order.

To achieve a desired particle size, a pulverized product is appropriately used, if necessary. Examples of the grinding method include a method of grinding by an air-stream grinding machine and a method using a hammer type grinding machine.

In the present specification, the "powder comprising an active ingredient" means an active ingredient (drug substance) that may be mixed with an excipient and/or an additive (e.g., additive acceptable for use as a pharmaceutical product such as sweetener, acidulant, flavor, dyes, antioxidant, stabilizer, surfactant and the like). The "granule containing an active ingredient" (sometimes to be referred to as "active ingredient granule") means a granule produced by granulating and drying the aforementioned powder comprising an active ingredient.

In the present specification, the "corn-derived pregelatinized starch" means a starch wherein a part or all of cornstarch is pregelatinized, which is obtained by a heat treatment, in water, of cornstarch free of chemical modification such as introduction of a substituent by a chemical reaction and the like. Examples thereof include pregelatinized starch wherein substantially all of cornstarch is pregelatinized and partly pregelatinized starch wherein a part of cornstarch is pregelatinized. Generally, the degree of pregelatinization of the partly pregelatinized starch is less than 30%, and is distinguished from that of pregelatinized starch having higher degree of pregelatinization. The degree of pregelatinization of the corn-derived pregelatinized starch to be used here is preferably not less than 50%, more preferably not less than 70%. The degree of pregelatinization can be measured by, for example, a glucoamylase method or an iodometric amperometric titration method.

As the starch wherein substantially all cornstarch is pregelatinized, commercially available AMICOL C (trade name) and the like can be specifically mentioned. AMICOL C here is a powder obtained by pregelatinizing cornstarch in water and rapidly drying the same.

Specific examples of the partly pregelatinized starch include commercially available PCS-PC-10, Graflow, Starch 1500 and the like. These partly pregelatinized starches are also powders obtained by partially pregelatinizing cornstarch in water, followed by drying.

In addition, viscous liquid starch obtained by dispersing cornstarch in water and heat-treating the same to cause pregelatinization of a part or all thereof can also be prepared and used.

In the present invention, as a binding solution to be used for producing a granule containing an active ingredient, an aqueous solution of the above-mentioned corn-derived pregelatinized starch and mannitol can be mentioned. For example, commercially available powdered corn-derived pregelatinized starch is dispersed in purified water heated to 50-100° C. at a concentration of 0.5-10%, preferably 0.5-3% (wt %), and mannitol is added thereto in a proportion of 10%-30%, preferably 10%-25%, more preferably 10%-20% (wt %), of the total weight of the binding solution. The resulting solution is used as a binding solution for granulation.

In addition, viscous liquid corn-derived pregelatinized starch obtained by dispersing cornstarch in water and heat-treating the same to cause pregelatinization of a part or all thereof can also be used. The proportion of pregelatinization of corn-derived pregelatinized starch obtained by heat treatment of cornstarch here is not particularly limited. For example, corn-derived pregelatinized starch wherein a part or all of cornstarch is pregelatinized is obtained by dispersing cornstarch in water in a proportion of 0.5-10%, preferably 0.5-3%, and performing a heat treatment at 60° C.-100° C. for 0.1-15 min. Preferably, corn-derived pregelatinized starch wherein a part or all of cornstarch is pregelatinized is obtained by treating at 62-95° C., more preferably 65° C.-85° C., particularly preferably 68-75° C., for preferably 0.5-10 min, more preferably 1-8 min, particularly preferably 2-6 min, and mannitol is added thereto in a proportion of 10%-30%, preferably 10%-25%, more preferably 10%-20%, of the total weight of the binding solution. The resulting solution is used as a binding solution.

It is preferable that mannitol corresponding to 10%-30%, preferably 10%-25%, more preferably 10-20%, of the total weight of the tablet be sprayed as the binding solution.

Examples of the disintegrant to be used in the present invention include cornstarch without heat treatment, hydroxypropylstarch which is hydroxypropylether of cornstarch, carmellose and crospovidone. From the aspects of disintegrability and compression moldability, cornstarch is preferable. While the average particle size of the disintegrant is not particularly limited, it is preferably 10-200 µm, more preferably 10-100 µm, further preferably 10-50 µm. To achieve a desired particle size, a pulverized product is appropriately used, if necessary. Examples of the grinding method include a method using an air-stream grinding machine and a method using a hammer type grinding machine.

The above-mentioned disintegrants can be used alone or in combination, and in a total proportion of 1-20 wt % relative to the total amount of the composition. When the disintegrant is cornstarch or hydroxypropylstarch, the disintegrant can be used in a proportion of preferably 4-20 wt %, more preferably 4-15 wt %, further preferably 8-12 wt %. On the other hand, when the disintegrant is carmellose or crospovidone, the disintegrant can be used in a proportion of preferably 1-10 wt %, more preferably 3-10 wt %, further preferably 4-8 wt %.

A part of the disintegrant can be added in advance to the active ingredient for the production of active ingredient granules (internal addition). In this case, the rest of the disintegrant is mixed with the active ingredient granules (later powder addition). In this case, 30%-100%, more preferably 50%-100%, of the disintegrant to be added is preferably added by later powder addition.

In addition, whole disintegrant can also be added after production of the active ingredient granules, without internal addition. A production method including production of granules by mixing whole disintegrant with an active ingredient (internal addition alone) cannot provide a tablet showing good disintegrability. However, later powder addition of a part or all of disintegrant as mentioned above can afford a tablet showing good disintegrability. It is most preferable to add the entire amount by later powder addition, without internal addition of the disintegrant.

In addition, a part of a disintegrant, a part of mannitol and/or other additives mentioned below may be blended as appropriate, and placebo granules are produced using a binding solution and used together with the active ingredient granules. Here, as the binding solution for producing the placebo granules, the aforementioned binding solution, or a binding solution containing corn-derived pregelatinized starch wherein a part or all of cornstarch is pregelatinized may be used. In addition, the binding solution for producing the active ingredient granules is as mentioned above.

In the present invention, the active ingredient before granulation may be mixed as appropriate with an excipient. That is, specific examples of the excipient to be mixed with the active ingredient in the first step of the production method of the present invention include water-soluble saccharides (mannitol, lactose, erythritol, maltitol, xylitol, sorbitol, purified sucrose etc.), which may be a mixture of one or more kinds of excipients selected from the group consisting of these specific examples. The excipient can also be added as appropriate in 1-65%, preferably 10-65%, of the total weight for the purpose of improving the disintegrability, solubility, moldability, tabletability, stability and the like. As the excipient, mannitol can be preferably mentioned, which is preferably added in 20-30% of the total weight.

While the time required for rapid disintegration in the oral cavity (disintegration time) is more or less different between individuals, in the present invention, it refers to complete disintegration within 40 seconds, preferably 35 seconds, more preferably 30 seconds, after placing a tablet in the oral cavity.

Experimentally, as the disintegration time, the time from placing a tablet in the oral cavity to complete disintegration thereof in the oral cavity is measured. After completion of the disintegration, the content is immediately spit out, and the mouth cavity is thoroughly washed with water. Therefore, "disintegration time of within 40 seconds" in the present invention means that the measurement value obtained by the aforementioned method is not longer than 40 seconds.

The active ingredient in the present invention is not particularly limited as long as it is a medicament with a large unit dose such as about 25% or more relative to the total weight of the tablet. For example, acetaminophen, ibuprofen, indomethacin, ethenzamide, droxidopa, levodopa, amoxicillin, cefalexin, erythromycin, clarithromycin and the like can be mentioned. Particularly, droxidopa and levodopa are preferable. While the particle size of the active ingredient is not particularly limited, the average particle size is preferably about 30-150 µm, more preferably about 50-100 µm.

The concentration of the active ingredient in the tablet of the present invention is generally not less than 25 wt % and not more than 80 wt %, preferably not less than 30 wt % and not more than 80 wt %, more preferably not less than 30 wt % and not more than 75 wt %, further preferably not less than 40 wt % and not more than 70 wt %, relative to the whole composition.

The average particle size of the active ingredient used in the present invention is generally 20-500 µm, preferably 20-250 µm, more preferably 20-100 µm. To achieve a desired particle size, a pulverized product is appropriately used, if necessary. Examples of the grinding method include a method of grinding by an air-stream grinding machine and a method using a hammer type grinding machine.

To produce the tablet which is rapidly disintegrated in an oral cavity of the present invention, for example, a mixture of an active ingredient and an excipient or an active ingredient is first granulated with a binding solution containing mannitol and corn-derived starch by a known method such as a fluidized bed granulation method, a spray dry method, a kneading method, a tumbling granulation method and the like. Preferably, a fluidized bed granulation method is adopted. The granules are appropriately dried and used for the next step.

Here, besides the described components, a small amount of additive acceptable for use for pharmaceutical products, such as sweetener, acidulant, flavor, dyes, antioxidant, stabilizer, surfactant and the like can be appropriately added, in addition to an excipient, to the active ingredient before granulation, for the object of molding, stabilization, improvement of taste and the like. These additives can be added in such an amount that does not adversely influence the disintegration time or hardness of the tablet which is rapidly disintegrated in an oral cavity.

Examples of the aforementioned sweetener include saccharides and sugar alcohols such as xylitol, erythritol, sorbitol, trehalose, glucose, sucrose and the like, and high sweetness sweeteners such as aspartame, sucralose, saccharin sodium, dipotassium glycyrrhizinate, thaumatin, stevia and the like. The sweetener can be added in not more than 2% of the total weight of the tablet.

Examples of the aforementioned flavor include strawberry, orange, pineapple, yogurt, peppermint, spearmint, menthol and the like, and the flavor can be added in not more than 2% of the total weight of the tablet.

Examples of the aforementioned acidulant include citric acid, malic acid, tartaric acid and the like, and the acidulant can be added in not more than 2% of the total weight of the tablet.

Examples of the aforementioned dyes include yellow ferric oxide, red ferric oxide and the like, and the dyes can be added in not more than 1% of the total weight of the tablet.

Examples of the aforementioned antioxidant include butylhydroxyanisole, dibutylhydroxytoluene, sodium pyrosulfite, ascorbic acid, erythorbic acid, tocopherol and the like, and the antioxidant can be added in not more than 2% of the total weight of the tablet.

Examples of the aforementioned stabilizer include glycerol, propylene glycol, L-arginine and the like, and the stabilizer can be added in not more than 2% of the total weight of the tablet.

Examples of the aforementioned surfactant include polysorbate 80, sodium lauryl sulfate, polyoxyethylene, hydrogenated castor oil and the like, and the surfactant can be added in not more than 2% of the total weight of the tablet.

Preferable examples of the additive include sweeteners such as aspartame, sucralose, acesulfame potassium and the like, acidulants such as citric acid, malic acid, tartaric acid and the like, and the like.

Then, at least one disintegrant selected from cornstarch hydroxypropylstarch, carmellose and crospovidone is mixed with the active ingredient granules obtained by drying the granules, whereby a pre-tableting composition can be obtained.

Alternatively, a pre-tableting composition is obtained by mixing active ingredient granules, which are obtained by granulating an active ingredient alone with a binding solution containing mannitol and corn-derived pregelatinized starch, placebo granules (granule not containing active ingredient) obtained by granulating an excipient such as mannitol and the like, which may contain the aforementioned additive as appropriate, with the aforementioned binding solution, and the above-mentioned disintegrant.

In addition, after granulation, the above-mentioned additive can also be added together with a disintegrant, and the kind and amount of the additive to be added are as mentioned above.

The pre-tableting composition, which is obtained in the above, can be tableted by any of an internal lubrication method including compression molding (tableting) after mixing a lubricant with it, and an external lubrication method including tableting while spraying a lubricant on a punch and a die, without mixing the lubricant with it in advance.

Tableting by an external lubrication method allowing attachment of a trace amount of a lubricant to the tablet surface is effective for achieving superior disintegrability. The amount of the lubricant to be blended is generally 0.5-5 wt % in the case of an internal lubrication method. The external lubrication method shows a lubrication effect with a smaller amount, and therefore, the amount is generally 0.05-1 wt %. Tableting can be performed using a suitable tableting machine such as a rotary tableting machine, a single tableting machine, an oil hydraulic pressing machine and the like.

The tableting pressure is preferably 6-18 kN when the tablet diameter is 8-10 mm.

The lubricant is not particularly limited in both the kind and the amount as long as they are in acceptable range for use for pharmaceutical products. Examples of usable lubricant include magnesium stearate, stearic acid, calcium stearate, sodium stearyl fumarate, talc, sucrose ester of fatty acid, talc, hydrogenated oil, carnauba wax and the like. Magnesium stearate is particularly preferable, since it shows a high lubrication effect with a small amount.

The tablet of the present invention characteristically shows a disintegration time within 40 seconds, preferably 35 seconds, more preferably 30 seconds, and an absolute hardness of 1.8 N/mm$^2$ or more, preferably 2.0 N/mm$^2$ or more. Accordingly, DHB (Disintegrating time-Hardness-Balance Index), which is an index showing the balance between disintegration time and hardness, is preferably not more than 18, more preferably not more than 15. The DHB here can be calculated as follows:

DHB=oral disintegration time (s)/absolute hardness (N/mm$^2$).

In the present specification, the absolute hardness is a value calculated by the following formula:

absolute hardness=tablet hardness (N)/cross section of tablet (mm$^2$).

Here, the hardness of a tablet is a pressure at which the tablet is broken when a pressure is applied in the diameter direction thereof, which is measured using a tablet hardness tester (TH-203 MP, manufactured by Toyama Sangyo Co., Ltd.).

The cross section of a tablet means a cross sectional area passing through the center of the tablet, i.e., a cross sectional area at the thickest part of the tablet. For example, when the tablet is flat without concaves and convexes: cross section of tablet (mm$^2$)=tablet diameter (mm)×tablet thickness (mm).

In addition, the tablet of the present invention shows friability of not more than 1%, preferably not more than 0.6%, and is hard to break even when a tablet automatic packaging machine is used. The friability is measured according to the tablet friability test described in the Japanese Pharmacopoeia Fifteenth Edition.

The shape of the tablet in the present invention is not particularly limited and may be a round-shaped tablet, an ellipse tablet, various irregularly-shaped tablets or the like. In addition, it may be a scored tablet with a separating line.

The present invention is explained in more detail in the following by referring to Examples and Comparative Examples, to which it is not necessarily limited.

EXAMPLES

Example 1

(Preparation of tablet of Example 1)

To heated purified water were added D-mannitol (200 g) and AMICOL C (7 g) to give a binding solution (1000 g) for active ingredient. Using Multiplex MP-01 (manufactured by POWREX CORPORATION), only the active ingredient was granulated with the above-mentioned binding solution for active ingredient to give active ingredient granules. Separately, to heated purified water was added AMICOL C (7 g) to give a binding solution (360 g) for placebo granules. Each component other than the active ingredient was charged in a container, and granulated using the above-mentioned binding solution for placebo granules to give placebo granules. Table 1 shows the composition of the mixture before the granulation step.

TABLE 1

| components | active ingredient granules | placebo granules |
| --- | --- | --- |
| droxidopa | 500 g | — |
| D-mannitol | — | 432 g |
| cornstarch | — | 88 g |
| anhydrous citric acid | — | 10 g |
| aspartame | — | 10 g |

The active ingredient granules (282.8 g), placebo granules (89.2 g), cornstarch (20.0 g) and sodium stearyl fumarate (8.0 g) were mixed, and compressed by Table Press TB-20H (manufactured by NPa SYSTEM CO., LTD.) at pressure 12 kN using a punch and a die both coated with a suspension of magnesium stearate in ethanol and dried, whereby flat tablets (diameter 10 mm) were obtained.

(Preparation of Tablet of Comparative Example 1)

The active ingredient granules (282.8 g) and placebo granules (109.2 g) prepared in the same manner as in Example 1, and sodium stearyl fumarate (8.0 g) were mixed, and compressed by Table Press TB-20H (manufactured by NPa SYSTEM CO., LTD.) at pressure 12 kN using a punch and a die both coated with a suspension of magnesium stearate in ethanol and dried, whereby flat tablets (diameter 10 mm) were obtained.

(Properties of Tablet)

The disintegration time and hardness of the samples of Example 1 and Comparative Example 1 were measured, and the results are shown in Table 2. Example 1 clearly showed fine disintegrability and high hardness as compared to Comparative Example 1, and showed superior properties as a tablet which is rapidly disintegrated in an oral cavity.

TABLE 2

|  | disintegration time (s) | hardness (N) |
|---|---|---|
| Example 1 | 33 | 92 |
| Comparative Example 1 | 48 | 71 |

Example 2

To heated purified water were added D-mannitol (4500 g) and AMICOL C (300 g) to give a binding solution (22500 g). Each component indicated in Table 3 was charged in FLO-COATER FLF-30 (manufactured by Freund Corporation), and granulated with the above-mentioned binding solution. After drying, the resulting granules (28440 g) and cornstarch (1500 g) were mixed, and the mixture was tableted by a rotary tableting machine and an external lubrication system (manufactured by Kikusui Seisakusho Ltd.) using a small amount of magnesium stearate as a lubricant at a tableting pressure of 15 kN, whereby tablets (diameter 10 mm, weight about 400 mg) were obtained. The content of magnesium stearate is about 0.4-0.8 mg per 200 tablets.

Droxidopa used here was micronized in advance, and used was that having an average particle size of 50-100 μm.

TABLE 3

| components | Example 2 |
|---|---|
| droxidopa | 15000 g |
| D-mannitol | 7080 g |
| cornstarch | 1500 g |
| aspartame | 75 g |

Example 3

To heated purified water were added D-mannitol (4500 g) and AMICOL C (300 g) to give a binding solution (22500 g). Each component indicated in Table 4 was charged in FLO-COATER FLF-30 (manufactured by Freund Corporation), and granulated using the above-mentioned binding solution. After drying, the resulting granules (26955 g) and cornstarch (3000 g) were mixed, and the mixture was tableted by a rotary tableting machine and an external lubrication system (manufactured by Kikusui Seisakusho Ltd.) using, in the same manner as in Example 2, magnesium stearate as a lubricant and a 10-mm-diameter R-surface punch at a tableting pressure of 12 kN, whereby tablets (weight about 400 mg) were obtained.

Droxidopa used here were that micronized in advance in the same manner as in Example 2.

TABLE 4

| components | Example 3 |
|---|---|
| droxidopa | 15000 g |
| D-mannitol | 7080 g |
| aspartame | 75 g |

(Properties of Tablet)

The tablet properties of the samples of Examples 2 and 3 are shown in Table 5. The friability was measured according to the tablet friability test described in the Japanese Pharmacopoeia the Fifteenth Edition. When the whole disintegrant was added by later powder addition, all the samples showed sufficient tablet strength and good disintegrability, and Example 3 was more superior in disintegrability.

TABLE 5

|  | Example 2 | Example 3 |
|---|---|---|
| thickness (mm) | 4.68 | 4.72 |
| hardness (N) | 89.4 | 91.9 |
| absolute hardness (N/mm$^2$) | 2.20 | 2.23 |
| friability (%) | 0.47 | 0.49 |
| disintegration time (s) | 32 | 23 |

Example 4

The resulting granules were obtained in the same manner as in Example 3. Each disintegrant indicated in Table 7 was added to 10 wt % of the whole and mixed in the proportion indicated in Table 6. The mixture was compressed by Table Press TB-20H (manufactured by NPa SYSTEM CO., LTD.) at pressure 12 kN using a punch and a die both coated with a suspension of magnesium stearate in ethanol and dried, whereby flat tablets (diameter 10 mm, weight about 400 mg) were obtained. The disintegration time, thickness and hardness of the tablets were measured, and the results are shown in Table 7.

TABLE 6

| resulting granules | 18.0 g |
|---|---|
| disintegrant | 2.0 g |
| total | 20.0 g |

TABLE 7

| disintegrant | oral disintegration time (s) | hardness (N) | thickness (mm) | absolute hardness (N/mm$^2$) | DHB (disintegration time/ absolute hardness) |
|---|---|---|---|---|---|
| cornstarch | 24 | 87.0 | 3.81 | 2.3 | 10.5 |
| hydroxypropyl-starch | 25 | 90.3 | 3.80 | 2.4 | 10.5 |

TABLE 7-continued

| disintegrant | oral disintegration time (s) | hardness (N) | thickness (mm) | absolute hardness (N/mm$^2$) | DHB (disintegration time/ absolute hardness) |
|---|---|---|---|---|---|
| L-HPC | 44 | 84.3 | 3.89 | 2.2 | 20.3 |
| carboxymethyl-starch Na | 67 | 68.3 | 3.84 | 1.8 | 37.7 |
| croscarmellose Na | 97 | 77.7 | 3.84 | 2.0 | 47.9 |
| carmellose Ca (CMC-Ca) | 67 | 62.3 | 3.87 | 1.6 | 41.6 |
| partially pregelatinized starch | 61 | 70.0 | 3.87 | 1.8 | 33.7 |
| no addition | 92 | 67.0 | 3.45 | 1.9 | 34.5 |

As a result, when cornstarch or hydroxypropylstarch from among the disintegrants generally used was added by later powder addition, the balance between tablet strength and disintegrability was superior.

Example 5

In the same manner as in Example 4 except that the tableting pressure was set to 15 kN, each disintegrant indicated in Table 9 was added at the proportion indicated in Table 8 to 10 wt % of the whole, mixed and prepared into tablets. The disintegration time, thickness and hardness of the tablet was measured, and the results are shown in Table 9.

TABLE 8

| resulting granules | 19.2 g |
|---|---|
| disintegrant | 0.8 g |
| total | 20.0 g |

TABLE 9

| disintegrant | oral disintegration time (s) | hardness (N) | thickness (mm) | absolute hardness (N/mm$^2$) | DHB |
|---|---|---|---|---|---|
| crospovidone | 26 | 78.3 | 3.85 | 2.0 | 13.0 |
| carmellose (CMC) | 21 | 78.0 | 3.79 | 2.1 | 10.0 |

By the addition of 4% of crospovidone or carmellose as a disintegrant, good tablet which is rapidly disintegrated in an oral cavity could be obtained.

Example 6

(Tablet which is Rapidly Disintegrated in an Oral Cavity (400 Mg Tablet) Containing Levodopa and Carbidopa as Active Ingredients)

To heated purified water were added D-mannitol (61.2 g) and AMICOL C (4.8 g) to give a binding solution (306 g). Each component indicated in Table 10 was charged in Multiplex MP-01 (manufactured by POWREX CORPORATION), and granulated with the above-mentioned binding solution. After drying, the resulting granules (70.6 g), cornstarch (6.4 g) and crospovidone (3.0 g) were mixed, and the mixture was compressed by Table Press TB-20H (manufactured by NPa SYSTEM CO., LTD.) at pressure 12 kN using a punch and a die both coated with a suspension of magnesium stearate in ethanol and dried, whereby flat tablets (diameter 10 mm) were obtained.

TABLE 10

| | components | Example 6 (per 400 mg tablet) |
|---|---|---|
| powder containing active ingredient | levodopa | 250.0 mg |
| | carbidopa | 25.0 mg |
| | D-mannitol | 23.0 mg |
| binding solution | AMICOL C | 4.0 mg |
| | D-mannitol | 51.0 mg |
| disintegrant | cornstarch | 32.0 mg |
| | crospovidone | 15.0 mg |
| lubricant | magnesium stearate | e.q. |

Example 7 and Example 8

(Tablet Which is Rapidly Disintegrated in an Oral Cavity (333 mg Tablet) Containing Ethenzamide as Active Ingredient)

To heated purified water were added D-mannitol (60.0 g) and AMICOL C (6.0 g) to give a binding solution (300.0 g). Each component indicated in Table 11 was charged in Multiplex MP-01 (manufactured by POWREX CORPORATION), and granulated with the above-mentioned binding solution. After drying, crospovidone (3.0 g) was added to the resulting granules (63.6 g) (Example 7), and cornstarch (6.4 g) was added to the resulting granules (63.6 g) (Example 8), and the mixture was compressed by Table Press TB-20H (manufactured by NPa SYSTEM CO., LTD.) at pressure 10 kN using a punch and a die both coated with a suspension of magnesium stearate in ethanol and dried, whereby flat tablets (diameter 10 mm) were obtained.

TABLE 11

| | components | Example 7 (per 333 mg tablet) | Example 8 (per 350 mg tablet) |
|---|---|---|---|
| powder containing active ingredient | ethenzamide | 200.0 mg | 200.0 mg |
| | D-mannitol | 74.0 mg | 74.0 mg |
| binding solution | AMICOL C | 4.0 mg | 4.0 mg |
| | D-mannitol | 40.0 mg | 40.0 mg |
| disintegrant | crospovidone | 15.0 mg | — |
| | cornstarch | — | 32.0 mg |
| lubricant | magnesium stearate | e.q. | e.q. |

Example 9

(Tablet which is Rapidly Disintegrated in an Oral Cavity (260 Mg Tablet) Containing Ibuprofen as Active Ingredient)

To heated purified water were added D-mannitol (80.0 g) and AMICOL C (4.0 g) to give a binding solution (400.0 g). Each component indicated in Table 12 was charged in Multiplex MP-01 (manufactured by POWREX CORPORATION), and granulated with the above-mentioned binding solution. After drying, the resulting granules (46.0 g) and cornstarch (6.0 g) were mixed, and the mixture was compressed by Table Press TB-20H (manufactured by NPa SYSTEM CO., LTD.) at pressure 8 kN using a punch and a die both coated with a suspension of magnesium stearate in ethanol and dried, whereby flat tablets (diameter 9 mm) were obtained.

TABLE 12

| | components | Example 9 (per 260 mg tablet) |
|---|---|---|
| powder containing active ingredient | ibuprofen | 100.0 mg |
| | D-mannitol | 80.5 mg |
| | carmellose | 7.5 mg |
| binding solution | AMICOL C | 2.0 mg |
| | D-mannitol | 40.0 mg |
| disintegrant | cornstarch | 30.0 mg |
| lubricant | magnesium stearate | e.q. |

Example 10

(Oral Disintegration Time and Strength of Tablet which is Rapidly Disintegrated in an Oral Cavity)

The oral disintegration time, tablet hardness and thickness were measured, and the absolute hardness and DHB were calculated. The obtained tablets were all superior in the disintegrability in the oral cavity, and the object orally disintegrating tablet having good balance between hardness and disintegration was obtained.

TABLE 13

| disintegrant | oral disintegration time (s) | hardness (N) | thickness (mm) | absolute hardness (N/mm$^2$) | DHB |
|---|---|---|---|---|---|
| Example 6 | 28 | 91.3 | 4.16 | 2.2 | 12.8 |
| Example 7 | 19 | 129.0 | 3.73 | 3.5 | 5.5 |
| Example 8 | 29 | 136.0 | 3.80 | 3.6 | 8.1 |
| Example 9 | 35 | 85.3 | 3.41 | 2.8 | 12.6 |

Example 11

The oral disintegration time and strength of droxidopa tablet which is rapidly disintegrated in an oral cavity (400 mg tablet) were measured.
<Preparation of Binding Solution>

Example 11-1

To heated purified water were added D-mannitol (60.0 g) and AMICOL C (4.0 g) to give a binding solution (300.0 g).

Example 11-2

To heated purified water were added D-mannitol (52.0 g) and AMICOL C (4.0 g) to give a binding solution (260.0 g).

Example 11-3

To heated purified water were added D-mannitol (48.0 g) and AMICOL C (4.0 g) to give a binding solution (240.0 g).
<Granulation>

Each component indicated in Table 14 was charged in Multiplex MP-01 (manufactured by POWREX CORPORATION), and granulated with the above-mentioned binding solution and dried.
<Preparation of Granule for Tableting>

Example 11-1

The resulting granules (18.0 g) were mixed with cornstarch (2.0 g).

Example 11-2

The resulting granules (17.8 g) were mixed with cornstarch (2.2 g).

Example 11-3

The resulting granules (17.6 g) were mixed with cornstarch (2.4 g).
<Tableting>

The granules for tableting prepared in the above were respectively compressed by Table Press TB-20H (manufactured by NPa SYSTEM CO., LTD.) at pressure 12 kN using a punch and a die both coated with a suspension of magnesium stearate in ethanol and dried, whereby flat tablets (diameter 10 mm) were obtained.

The tablets of Example 11-1, Example 11-2 and Example 11-3 were measured for the oral disintegration time, tablet hardness and thickness, and the absolute hardness and DHB were calculated. The results are shown in Table 14 and Table 15.

TABLE 14

| | components | Example 11-1 | Example 11-2 | Example 11-3 |
|---|---|---|---|---|
| powder containing active ingredient | droxidopa | 160.0 mg | 240.0 mg | 280.0 mg |
| | D-mannitol | 135.0 mg | 59.0 mg | 19.0 mg |
| | aspartame | 1.0 mg | 1.0 mg | 1.0 mg |
| binding solution | AMICOL C | 4.0 mg | 4.0 mg | 4.0 mg |
| | D-mannitol | 60.0 mg | 52.0 mg | 48.0 mg |
| disintegrant | cornstarch | 40.0 mg | 44.0 mg | 48.0 mg |
| lubricant | magnesium stearate | e.q. | e.q. | e.q. |

TABLE 15

| disintegrant | oral disintegration time (s) | hardness (N) | thickness (mm) | absolute hardness (N/mm$^2$) | DHB |
|---|---|---|---|---|---|
| Example 11-1 | 16 | 91.3 | 3.84 | 2.4 | 6.7 |
| Example 11-2 | 19 | 80.0 | 3.82 | 2.1 | 9.1 |
| Example 11-3 | 23 | 78.7 | 3.80 | 2.1 | 11.1 |

The obtained tablets were all superior in the disintegrability in the oral cavity, and the object orally disintegrating tablet having good balance between hardness and disintegration was obtained.

Comparative Example 2

Tablets containing droxidopa were prepared by granulating with a mannitol-free binding solution. The results are shown below.

To heated purified water was added AMICOL C (32.0 g) to give a binding solution (1920 g). Each component indicated in the following Table 16 was charged in Multiplex MP-01 (manufactured by POWREX CORPORATION), and granulated with the above-mentioned binding solution. After drying, the granules were tableted by a rotary tableting machine and an external lubrication system (manufactured by Kikusui Seisakusho Ltd.) using, in the same manner as in Example 2, magnesium stearate as a lubricant and a 10-mm-diameter R-surface punch at a tableting pressure of 12 kN, whereby tablets (weight about 400 mg) were obtained. In addition, when the tableting pressure was increased to 15 kN, tableting trouble was developed, and tableting could not be performed.

Droxidopa used here was that micronized in advance in the same manner as in Example 2. The disintegration time, thickness and hardness of the tablets were measured, and the results are shown in Table 17.

TABLE 16

| component | Comparative Example 2 |
|---|---|
| droxidopa | 1600.0 g |
| D-mannitol | 1411.2 g |
| cornstarch | 140.8 g |
| aspartame | 16.0 g |

TABLE 17

| | Disintegration time (s) | hardness (N) | thickness (mm) | absolute hardness (N/mm$^2$) | DHB |
|---|---|---|---|---|---|
| Comparative Example 2 | 30 | 64 | 4.77 | 1.5 | 19.5 |

The starting materials used in the Examples in the present specification are shown below.
1. D-mannitol (Kyowa Hakko Kogyo Co., Ltd.)
2. cornstarch (trade name: cornstarch(XX16)W, NIHON SHOKUHIN KAKO CO., LTD.)
3. magnesium stearate (St-Mg, Taihei Chemical Industrial Co., Ltd.)
4. sodium stearyl fumarate (trade name: PRUV, JRS Pharma LP)
5. pregelatinized starch (trade name: AMICOL C, NIPPON STARCH CHEMICAL CO., LTD.)
6. anhydrous citric acid (San-Ei Gen F.F.I., Inc.)
7. aspartame (Ajinomoto Co., Inc.)
8. crospovidone (trade name: Kollidone CL, BASF Japan)
9. sodium carboxymethyl starch (trade name: Primojel, GOKYO TRADING CO., LTD.)
10. low-substituted hydroxypropylcellulose (L-HPC, trade name: LH-21, Shin-Etsu Chemical Co., Ltd.)
11. croscarmellose sodium (trade name: Ac-Di-sol, GOKYO TRADING CO., LTD.)
12. carmellose calcium (CMC-Ca, trade name: ECG-505, GOTOKU CHEMICAL CO., LTD.)
13. partly pregelatinized starch (trade name: PCS-PC-10, Asahi Kasei Corporation)
14. rice starch (trade name: Micro Pearl, Shimada Kagaku Kogyo K.K.)
15. carmellose (CMC) (trade name: NS-300, GOTOKU CHEMICAL CO., LTD.)
16. hydroxypropylstarch: HPS-101(W) (Freund Corporation)

Industrial Applicability

The present invention has made it possible to provide an tablet which is rapidly disintegrated in an oral cavity containing an active ingredient at a high concentration, and having both good disintegrability in the oral cavity and tablet strength sufficient to apply automatic packaging machines, and a production method thereof.

The invention claimed is:

1. A tablet, which is rapidly disintegrated in an oral cavity, comprising (a) an active ingredient selected from the group consisting of acetaminophen, ibuprofen, indomethacin, ethenzamide, droxidopa, levodopa, amoxicillin, cefalexin, erythromycin, and clarithromycin in not less than 25% of the total weight, (b) mannitol, (c) corn-derived pregelatinized starch, and (d) at least one disintegrant selected from the group consisting of cornstarch, hydroxypropylstarch, carmellose and crospovidone, wherein the tablet is obtained by compression molding of a mixture comprising a granule obtainable by granulating a powder comprising the active ingredient with a binding solution comprising mannitol and corn-derived pregelatinized starch, and at least one disintegrant.

2. The tablet, which is rapidly disintegrated in an oral cavity, according to claim 1, further having a disintegration time of within 40 seconds and an absolute hardness of 1.8 N/mm$^2$ or more, which is obtained by compression molding of a mixture of a granule produced by granulating a powder comprising the active ingredient with a binding solution comprising mannitol and corn-derived pregelatinized starch, and at least one disintegrant selected from the group consisting of cornstarch, hydroxypropylstarch, carmellose and crospovidone.

3. The tablet, which is rapidly disintegrated in an oral cavity, according to claim 1, wherein the absolute hardness is 2.0 N/mm$^2$ or more.

4. The tablet, which is rapidly disintegrated in an oral cavity, according to claim 1, wherein the disintegrant is cornstarch or hydroxypropylstarch.

5. The tablet, which is rapidly disintegrated in an oral cavity, according to claim 1, wherein the powder comprises the active ingredient and mannitol.

6. The tablet, which is rapidly disintegrated in an oral cavity, according to claim 1, comprising the active ingredient in not less than 40% of the total weight.

7. The tablet, which is rapidly disintegrated in an oral cavity, according to claim 6, comprising the active ingredient in 40%-70% of the total weight.

8. The tablet, which is rapidly disintegrated in an oral cavity, according to claim 1, wherein the active ingredient is droxidopa or levodopa.

9. A method of producing a tablet, which is rapidly disintegrated in an oral cavity, according to claim 1, which method comprises the following steps:
(1) a step of granulating a powder comprising the active ingredient with a binding solution comprising mannitol and corn-derived pregelatinized starch to produce a granule comprising the active ingredient;
(2) a step of mixing the granule comprising the active ingredient obtained in (1) with at least one disintegrant selected from the group consisting of cornstarch, hydroxypropylstarch, carmellose and crospovidone; and (3) a step of compression molding a pre-tableting composition comprising the mixture obtained in (2).

10. A method of producing the tablet, which is rapidly disintegrated in an oral cavity, according to claim 4, which method comprises the following steps:
   (1) a step of granulating a powder comprising the active ingredient with a binding solution comprising mannitol and corn-derived pregelatinized starch to produce a granule comprising the active ingredient;
   (2) a step of mixing the granule comprising the active ingredient obtained in (1) with a disintegrant which is cornstarch or hydroxypropylstarch; and
   (3) a step of compression molding of the mixture obtained in (2).

11. The method according to claim 9, wherein a disintegration time of the tablet, which is rapidly disintegrated in an oral cavity, is 40 seconds or less, and an absolute hardness thereof is 1.8 N/mm$^2$ or more.

12. The method according to claim 9, comprising a step of compression molding by an external lubrication method.

13. The method according to claim 9, wherein the absolute hardness of the tablet, which is rapidly disintegrated in an oral cavity, is 2.0 N/mm$^2$ or more.

14. The method according to claim 9, wherein the active ingredient is droxidopa or levodopa.

15. The tablet, which is rapidly disintegrated in an oral cavity, according to claim 1, wherein the granule does not contain a disintegrant selected from the group consisting of cornstarch, hydroxypropylstarch, carmellose, and crospovidone.

16. The method according to claim 9, wherein the granule does not contain a disintegrant selected from the group consisting of cornstarch, hydroxypropylstarch, carmellose, and crospovidone.

17. The tablet, which is rapidly disintegrated in an oral cavity, according to claim 1, which is obtained by the following steps:
   (1) a step of granulating a powder comprising the active ingredient with a binding solution comprising mannitol and corn-derived pregelatinized starch to produce a granule comprising the active ingredient;
   (2) a step of mixing the granule comprising the active ingredient obtained in (1) with at least one disintegrant selected from the group consisting of cornstarch, hydroxypropylstarch, carmellose, and crospovidone; and
   (3) a step of compression molding a pre-tableting composition comprising the mixture obtained in (2).

18. The tablet, which is rapidly disintegrated in an oral cavity, according to claim 1, wherein the active ingredient is droxidopa.

19. The tablet, which is rapidly disintegrated in an oral cavity, according to claim 7, wherein the active ingredient is droxidopa.

20. The method according to claim 9, wherein the active ingredient is droxidopa.

* * * * *